United States Patent [19]

Kim

[11] 4,161,611

[45] Jul. 17, 1979

[54] PROCESS FOR THE PRODUCTION OF 2-METHOXY-3,6-DICHLOROBENZOIC ACID

[75] Inventor: Dong-Whee Kim, Deerfield, Ill.

[73] Assignee: Veesicol Chemical Corporation, Chicago, Ill.

[21] Appl. No.: 868,091

[22] Filed: Jan. 9, 1978

Related U.S. Application Data

[63] Continuation of Ser. No. 654,249, Feb. 23, 1976, abandoned.

[51] Int. Cl.² ............................................. C07C 65/08
[52] U.S. Cl. ..................................... 562/474; 260/187
[58] Field of Search ....................... 562/474, 475, 478; 260/187

[56] References Cited

U.S. PATENT DOCUMENTS

| | | | |
|---|---|---|---|
| 2,489,423 | 11/1949 | Lawson | 568/774 |
| 2,547,679 | 4/1951 | Wolfe | 260/613 |
| 2,665,313 | 1/1954 | Lisk | 568/737 |
| 2,813,906 | 1/1957 | McPherson | 260/586 |
| 3,013,054 | 12/1961 | Richter | 520/474 |
| 3,013,056 | 12/1961 | Richter | 520/474 |
| 3,013,057 | 12/1961 | Richter | 520/474 |
| 3,013,058 | 12/1961 | Richter | 520/474 |

OTHER PUBLICATIONS

Moller, "Chem. of Org. Comp.", pp. 542, 544, 3rd Edition, Saunders (1965).

*Primary Examiner*—Norman Morgenstern
*Attorney, Agent, or Firm*—Robert J. Schwarz; Dietmar Olesch

[57] ABSTRACT

This invention discloses a process for the production of 2-methoxy-3,6-dichlorobenzoic acid which comprises reacting 2-amino-3,6-dichlorobenzoic acid with nitrous acid to form the corresponding diazonium salt, hydrolyzing the diazonium salt to form 2-hydroxy-3,6-dichlorobenzoic acid and methylating said hydroxy acid.

12 Claims, No Drawings

PROCESS FOR THE PRODUCTION OF 2-METHOXY-3,6-DICHLOROBENZOIC ACID

This is a continuation of application Ser. No. 654,249 filed Feb. 23, 1976, now abandoned.

The present invention relates to a new chemical process. More specifically this invention relates to a process for preparing the compound 2-methoxy-3,6-dichlorobenzoic acid.

The compound 2-methoxy-3,6-dichlorobenzoic acid is a valuable herbicide and is used in commerce for the control of a variety of undesirable vegetation. The prior art discloses in U.S. Pat. No. 3,013,054 that the 2-methoxy-3,6-dichlorobenzoic acid is prepared from 1,2,4-trichlorobenzene in a three-stage process. The trichlorobenzene is first converted to 2,5-dichlorophenol with methanol and sodium hydroxide. The phenol is then treated with carbon dioxide under pressure to yield 2-hydroxy-3,6-dichlorobenzoic acid. The hydroxy acid is then methylated with dimethyl sulfate or methyl chloride to yield the desired product.

The prior art process, however, suffers from the disadvantage that the desired intermediate phenol forms as a mixture of isomers which is difficult to separate.

It has now been found that the valuable compound 2-methoxy-3,6-dichlorobenzoic acid can be readily prepared by a novel process wherein undesirable isomeric intermediates are avoided.

Accordingly, one embodiment of the present invention resides in a process for preparing 2-methoxy-3,6-dichlorobenzoic acid which comprises (a) reacting 2-amino-3,6-dichlorobenzoic acid with nitrous acid to form the corresponding diazonium salt; (b) hydrolyzing said diazonium salt to form 2-hydroxy-3,6-dichlorobenzoic acid; and (c) methylating the hydroxy group of said hydroxy acid.

The starting material 2-amino-3,6-dichlorobenzoic acid employed in the process of the present invention is a known compound and is produced as a major by-product in the production of the commercial compound 3-amino-2,5-dichlorobenzoic acid.

The first step of the process of the present invention wherein 2-amino-3,6-dichlorobenzoic acid is reacted with nitrous acid can be conveniently carried out by dissolving the benzoic acid in a suitable inert reaction medium such as a lower alkanol or water and thereafter preparing the nitrous acid in situ by combining a nitrosating agent and a mineral acid. When an aqueous reaction medium is utilized, an alkali metal salt of the benzoic acid can be utilized for improved solubility.

Suitable nitrosating agents which can be utilized in the process of the present invention include all of the commonly known nitrosating agents such as nitrous fumes, inorganic nitrites, such as, for example, alkali metal nitrites, e.g., sodium nitrite and potassium nitrite, and organic nitrites, such as, for example, lower alkyl nitrites, e.g., methyl nitrite, ethyl nitrite, propyl nitrite, isopropyl nitrite, n-butyl nitrite, sec-butyl nitrite, isobutyl nitrite, amyl nitrite, sec-amyl nitrite, isoamyl nitrite, and the like, the isoamyl nitrite being particularly suitable. Suitable acids employed in the diazotization include mineral acids, such as, for example, hydrochloric acid and sulfuric acid, lower alkanoic acids, such as, for example, acetic acid, propionic acid, butanoic acid, and perhalo (lower) alkanoic acids, such as, for example, trichloroacetic acid, trifluoroacetic acid, and trifluorobutanoic acid, and the mixtures thereof. Suitable organic solvents utilized in the reaction include aliphatic alkanols, such as, for example, methanol, ethanol, propanol, tetrahydrofuran, carbon tetrachloride, methyl cyclohexane, tetrachloroethylene, and the like. Suitable alkali metal hydroxides include sodium hydroxide and potassium hydroxide.

Although the diazotization can be effected satisfactorily with a minimum of one mole of a nitrosating agent for each mole of the 2-amino-3,6-dichlorobenzoic acid, it is desirable to use an excess of the nitrosating agent up to about 2 moles of the nitrosating agent for each mole of the starting compound. During the diazotization, the reaction temperature is maintained below 8° C., and it is preferred to maintain the temperature between about $-20°$ and about 5° C. The duration of the reaction will in general be from about 5 minutes to about 2 hours, the preferred duration being between about 10 minutes to about 1 hour.

The nitrous acid, as indicated, is formed upon combining a nitrosating agent with a mineral acid. At least two moles of the mineral acid per mole of nitrosating agent are used for this purpose.

It can be seen that a further embodiment of the first step of the process of the present invention comprises reacting a molar amount of 2-amino-3,6-dichlorobenzoic acid dissolved in an inert, water-miscible organic reaction medium with from 1 to 2 molar amounts of nitrous acid at a temperature of from about $-20°$ to about 5° C., said nitrous acid being prepared in situ by adding from 1 to 2 molar amounts of a nitrosating agent and from 2 to 20 molar amounts of a mineral acid.

The diazonium intermediate thus prepared is hydrolyzed in an excess of water and preferably in the presence of a strong mineral acid to the 2-hydroxy-3,6-dichlorobenzoic acid intermediate. Hydrolysis is conveniently effected at temperatures of from about 30° to 175° C., preferably from about 85° to about 155° C. or at the reflux temperature of the mixture. Suitable acid catalysts utilized in the hydrolysis reaction include mineral acids, such as, for example, sulfuric acid and hydrochloric acid. The duration of hydrolysis will in general be from about 30 minutes to about 35 hours, depending upon the temperature and the catalyst, if any, utilized.

In a preferred embodiment the hydrolysis is carried out in water and sulfuric acid. After the reaction is completed, the 2-hydroxy-3,6-dichlorobenzoic acid can be recovered upon extraction with ether or other standard techniques. The extract can then be purified if desired by washing and the like and can then be recovered upon evaporation of the solvent.

The 2-hydroxy-3,6-dichlorobenzoic acid is then methylated to form the desired 2-methoxy-3,6-dichlorobenzoic acid. This methylation can be carried out using methyl chloride or, in the alternative, dimethyl sulfate as the methylating agent.

Generally this reaction step can be carried out by dissolving a molar amount of 2-hydroxy-3,6-dichlorobenzoic acid in an aqueous basic reaction medium and adjusting the pH to above about 10, adding at least 2 molar amounts of methyl chloride to the reaction mixture at a pressure of from about 50 to about 150 pounds per square inch and heating the reaction mixture at a temperature of from about 75° to about 150° C.

In a preferred embodiment of the process of the present invention, the 2-hydroxy-3,6-dichlorobenzoic acid is methylated with methyl chloride in an aqueous medium which has a pH greater than about 10 to produce the desired 2-methoxy-3,6-dichlorobenzoic acid. The pH of the reaction mixture is critical to the successful use of methyl chloride for the methylation of 2-hydroxy-3,6-dichlorobenzoic acid. Indeed, if the pH of the reaction mixture is allowed to drop to 10 or below, the reaction produces large amounts of undesired by-products and a product of relatively low purity. If the pH of the reaction mixture is considerably lower than 10, such as 7 or lower, then the reaction stops or proceeds at such a slow rate as to be undetectable or impractical.

At least two moles of metal base are used in aqueous solution to treat each mole of 2-hydroxy-3,6-dichlorobenzoic acid employed. Suitable metal bases are sodium hydroxide, potassium hydroxide, sodium carbonate, potassium carbonate, calcium hydroxide, magnesium hydroxide, and the like. When the minimum amount of base has been added to form the metal salts of the carboxy and phenolic groups in the 2-hydroxy-3,6-dichlorobenzoic acid, further metal base is added to bring the pH of the solution above 10. While the reaction proceeds satisfactorily in solutions which have pH values above 10, a large excess of alkali metal base is not necessary. The reaction can be carried out at pH values of 10 or higher. Nevertheless, it is preferred that the pH of the reaction mixture be maintained between about 10 and 12, since the higher pH value reaction mixtures are not beneficial and there is no need to use them in this reaction. Furthermore, there is a tendency when the pH of the reaction mixture is above 12 for the information of undesired by-products.

The desired pH of the reaction medium can be maintained during reaction by adding small amounts of metal base as required. While the aqueous medium in the method of this invention will ordinarily comprise water alone as the solvent, other solvents or diluents can also be used in addition to the water.

After the aqueous metal salt solution of the 2-hydroxy-3,6-dichlorobenzoic acid has been prepared, methyl chloride gas is introduced into the reaction vessel, suitably under pressure. The exact pressure to be used will largely be determined by the reaction temperature and other factors. A convenient pressure range has been found to be from about 50 to about 150 pounds per square inch gauge. Pressures higher than 150 pounds are operable and produce results comparable to those obtained at the lower pressures; but, since there is no need to use these higher pressures, it is satisfactory to operate within the pressure range previously stated.

The precise temperature at which the reaction is carried out is not critical, but it is convenient to employ temperatures in the range from about 75° to about 150° C. A particularly convenient and preferred temperature range is from about 80° to about 100° C. It has been found that vigorous and efficient agitation of the reaction mixture favors the formation of the desired product in good yield.

The reaction is continued until about two moles of methyl chloride have reacted for each mole of 2-hydroxy-3,6-dichlorobenzoic acid charged. The reaction mixture at this point will consist of a mixture of the metal salt of 2-methoxy-3,6-dichlorobenzoic acid and some methyl ester of 2-methoxy-3,6-dichlorobenzoic acid. It is therefore necessary to hydrolyze any methyl ester that is formed. This can be accomplished by treating the reaction mixture with additional metal base. The reaction mixture is heated, preferably at reflux temperature, to complete the hydrolysis.

The desired 2-methoxy-3,6-dichlorobenzoic acid can then be separated from the reaction mixture by acidification. Mineral acids such as hydrochloric acid, sulfuric acid, and the like are most conveniently used for the acidification. The reaction mixture can be acidified to a pH of about 1, at which point the desired product will crystallize out of solution. It can be recovered by filtration or centrifugation and washed with water. The 2-methoxy-3,6-dichlorobenzoic acid obtained in this manner will be quite pure and can be used directly for pesticidal purposes without further purification. Drying of the product as in a forced-air dryer, for example, is all that is required. However, if a very pure product is desired, the solid can be recrystallized from a suitable solvent such as pentane to give white crystals, melting point 114°–116° C.

As previously indicated, the methylation can also be effected with dimethyl sulfate. This methylation is carried out in an aqueous solution, which is prepared by treating each mole of 2-hydroxy-3,6-dichlorobenzoic acid with at least 2 moles of an alkali metal hydroxide dissolved in water. Alkali metal hydroxides such as sodium hydroxide and potassium hydroxide are suitable. Although the reaction can be effected satisfactorily with a minimum of 2 moles of alkali metal hydroxide for each mole of the 2-hydroxy-3,6-dichlorobenzoic acid, it is desirable to use an excess of the alkali metal hydroxide. The alkali metal salt of the 2-hydroxy acid has limited solubility in water, and the use of an excess of up to about 5 moles of alkali metal hydroxide, for example, for each mole of the 2-hydroxy acid enhances solubility and avoids the use of large volumes of water. A ratio of about 4 moles of alkali metal hydroxide to each mole of the hydroxy compound is preferred.

The 2-hydroxy-3,6-dichlorobenzoic acid intermediate in aqueous solution as its alkali metal salts is treated with a minimum of 1 mole of dimethyl sulfate for each mole of the starting material. In actual practice, the use of an excess of dimethyl sulfate is preferred. The compound dimethyl sulfate decomposes slightly in water, which makes somewhat less than the amount initially employed actually available for the reaction. Similarly, some esterification of the carboxylic acid group takes place while the primary reaction of methylation of the hydroxy group is being effected. Thus, an excess of dimethyl sulfate is suitably used, equivalent to up to about 5 moles of dimethyl sulfate for each mole of 2-hydroxy-3,6-dichlorobenzoic acid. A ratio of about 4 moles of dimethyl sulfate to each mole of the starting compound is prepared.

The dimethyl sulfate is suitable added to the reaction mixture in a constant stream, in portions, or dropwise as is most convenient for the particular apparatus in use. During the addition, it is desirable to maintain the reaction temperature at from about 10° to about 100° C., with external cooling if necessary. Although the process of the invention can be carried out satisfactorily at the upper ranges of reaction temperature indicated, improved yields are obtained by working at the lower temperatures. Reaction temperatures in the range from about 20° to about 50° C. are preferred during the process of adding the dimethyl sulfate. The reaction is satisfactorily carried out at atmospheric pressure, although super-atmospheric pressures can be used if desired.

After addition of all the dimethyl sulfate, the reaction mixture is heated at reflux temperature to complete the reaction. The actual time required to complete the reaction depends on a variety of factors, such as the temperature during the addition of dimethyl sulfate, the rate of addition, alkalinity of the solution, and the like. The reaction is ordinarily complete in a few hours. The reaction mixture is then treated with a fresh aqueous solution of alkali metal hydroxide and again refluxed for several hours to hydrolyze any carboxlic acid ester which may have formed as a competing reaction during the formation of methyl ether. About one-half mole of alkali metal hydroxide is suitably used for each mole of dimethyl sulfate used in the reaction.

The cooled reaction mixture is then acidified to Congo red indicator, and the precipitated 2-methoxy-3,6-dichlorobenzoic acid is filtered off. Although the crude acid so obtained is suitable for many herbicidal uses as such, it can be purified if desired. In a typical purification process, for example, the acid is dissolved in diethyl ether, and the ether solution is dried over a drying agent such as magnesium sulfate before it is filtered and the ether is removed by distillation. The residue is washed with cold pentane and is then dried, as in a vacuum oven, to yield the 2-methoxy-3,6-dichlorobenzoic acid as a crystalline solid.

In another embodiment of the process of the present invention the 2-methoxy-3,6-dichlorobenzoic acid can be prepared by reacting the diazonium intermediate with absolute methanol in an inert organic solvent, such as ethyl ether. In actual practice, the 2-amino-3,6-dichlorobenzoic acid is converted to the diazonium intermediate with the treatment with a nitrosating agent in a manner analogous to that described hereinabove. The resulting diazonium intermediate is precipitated from the reaction mixture by adding thereto an inert organic solvent, such as ethyl ether. The precipitate is recovered by conventional techniques such as filtration, and washed with an additional solvent. The recovered product is then dissolved in an excess of absolute methanol, and the solution is heated on a water bath until nitrogen ceases to evolve from the reaction system. The methanol is then stripped in vacuo from the reaction mixture to give a residue. The residue is extracted with an inert organic solvent, such as ethyl ether, dried, and filtered. Removal of the solvent gives the desired 2-methoxy-3,6-dichlorobenzoic acid.

The process of the present invention is more specifically illustrated in the following examples.

EXAMPLE 1

Preparation of 2-Methoxy-3,6-dichlorobenzoic Acid

A. Diazotization

2-Amino-3,6-dichlorobenzoic acid (50 g, 0.24 mole) is dissolved in water (1 l.) and 2 N sodium hyroxide (130 ml, 0.26 mole). Sodium nitrite (20 g, 0.28 mole) is added to the resulting solution, and the mixture is stirred until all of the added sodium nitrite dissolves. The resulting solution is then added in 25 ml portions with vigorous shaking to a solution of 6 N hydrochloric acid (200 ml) and water (100 ml), while maintaining the solution at about 0° C. utilizing an ice-salt bath. The reaction mixture is then stirred at about 0° C. for an additional hour to ensure completion of the reaction. After this time urea (0.3 g) is added to the reaction mixture.

B. Hydrolysis

Concentrated sulfuric acid (100 ml) and water (100 ml) are charged into a reaction flask equipped with a reflux condenser, thermometer, and mechanical stirrer. The solution is then heated with stirring to about 130° to 145° C. The chilled diazonium solution, prepared as described above, is added portionwise thereto, and the resulting mixture is heated with continuous stirring at 130° to 145° C. for a period of one hour. Water (200 ml) is added to the reaction flask, and the reaction mixture is again heated at about 130° to 145° C. for an additional 3 to 4 hours to ensure completion of the reaction. The cooled reaction mixture is extracted with ethyl ether, dried over anhydrous magnesium sulfate, and filtered. The ether is stripped from the filtrate to give a residue. The residue is recrystallized from benzene to give the desired 2-hydroxy-3,6-dichlorobenzoic acid.

C. Methylation

2-Hydroxy-3,6-dichlorobenzoic acid (44.4 g), prepared as described above, is dissolved in sodium hydroxide and water, making 189 ml of solution. This material is methylated by the addition of methyl chloride at 85° to 90° C. and 69 to 95 p.s.i.g. for 10 hours in a stirred stainless steel pressure vessel. During the reaction the pressure is held between 80 and 95 p.s.i.g. The pH is initially 13 to 14, but as the reaction commences the pH as measured by pH paper and a continuous flow meter drops. The pH is maintained during reaction in the range of 10 to 12 by the periodic addition of sodium hydroxide (7 ml, 50% NaOH). Methyl chloride (26.3 g) is injected into the pressure vessel in the course of the reaction. At the end of the 10-hour reaction period, any unused methyl chloride is vented, and sodium hydroxide (9.5 ml, 50% NaOH) is added for the hydrolysis. The charge is refluxed for 5½ hours, converting the esters to the desired 2-methoxy-3,6-dichlorobenzoic acid.

EXAMPLE 2

Preparation of 2-Methoxy-3,6-dichlorobenzoic Acid

A. Diazotization

2-Amino-3,6-dichlorobenzoic acid (50 g, 0.24 mole) is dissolved in water (1 l.) and 2 N sodium hydroxide (130 ml, 0.26 mole). Potassium nitrite (0.28 mole) is added to the solution, and the mixture is stirred until all of the added potassium nitrite dissolves. The resulting solution is then added in 25 ml portions with vigorous shaking to a solution of concentrated sulfuric acid (200 ml) and crushed ice (200 ml). The reaction mixture is maintained at about 0° C. for an additional hour to ensure completion of the reaction. After this time urea (0.3 g) is added to the reaction mixture.

B. Hydrolysis

Concentrated sulfuric acid (100 ml) and water (100 ml) are charged into a reaction flask equipped with a reflux condenser, thermometer, and mechanical stirrer. The solution is heated with stirring to about 130° to 145° C., and the chilled diazonium solution, prepared as described above, is added portionwise thereto. The resulting mixture is heated with continuous stirring at 130° to 145° C. for a period of one hour. After this time water (200 ml) is added into the reaction flask, and the reaction mixture is again heated at about 130° to 145° C. for an additional 3 to 4 hours to ensure completion of the reaction. The cooled reaction mixture is extracted with ethyl ether, dried over anhydrous magnesium sulfate, and filtered. The ether is stripped from the filtrate to give a residue. The residue is recrystallized from benzene to give the desired 2-hydroxy-3,6-dichlorobenzoic acid.

C. Methylation

2-Hydroxy-3,6-dichlorobenzoic acid (44.4 g), prepared as described above, is dissolved in sodium hydroxide and water, making 189 ml of solution. This material is methylated by the addition of methyl chloride at 85° to 90° C. and 60 to 95 p.s.i.g. for 10 hours in a stirred stainless steel pressure vessel. During the reaction the pressure is held between 80 and 95 p.s.i.g. The pH is initially 13 to 14, but as the reaction commences the pH as measured by pH paper and a continuous flow meter drops. The pH is maintained during the reaction in the range of 10 to 12 by the periodic addition of sodium hydroxide (7 ml, 50% NaOH). Methyl chloride (26.3 g) is injected into the pressure vessel in the course of the reaction. At the end of the 10-hour reaction period, any unused methyl chloride is vented, and sodium hydroxide (9.5 ml, 50% NaOH) is added for the hydrolysis. The charge is refluxed for 5½ hours, converting the esters to the desired 2-methoxy-3,6-dichlorobenzoic acid.

EXAMPLE 3

Preparation of 2-Methoxy-3,6-dichlorobenzoic Acid

A. Diazotization

2-Amino-3,6-dichlorobenzoic acid (50 g, 0.24 mole) is dissolved in water (1 l.) and 2 N sodium hydroxide (130 ml, 0.26 mole). Sodium nitrite (20 g, 0.28 mole) is added to the solution, and the mixture is stirred until all of the added sodium nitrite dissolves. The resulting solution is then added in 25 ml portions with vigorous shaking to a solution of 6 N hydrochloric acid (200 ml) and water (100 ml), while maintaining the solution of about 0° C. utilizing an ice-salt bath. The reaction mixture is stirred at about 0° C. for an additional hour to ensure completion of the reaction. After this time urea (0.3 g) is added to the reaction mixture.

B. Hydrolysis

About 200 ml of ethyl ether is added to the diazonium solution, prepared as described above, to effect precipitation of the diazonium salt. This salt is then recovered by filtration and washed with addition ether. The product is then dissolved in water (500 ml) and concentrated sulfuric acid (250 ml), and the resulting solution is heated with continuous stirring to about 35° to 45° C. for a period of about 36 hours. The cooled reaction mixture is extracted with ethyl ether, dried over anhydrous magnesium sulfate, and filtered. The ether is stirred from the filtrate to give a residue. The residue is recrystallized from benzene to give the desired 2-hydroxy-3,6-dichlorobenzoic acid.

C. Methylation

2-Hydroxy-3,6-dichlorobenzoic acid (44.4 g), prepared as described above, is dissolved in sodium hydroxide and water, making 189 ml of solution. This material is methylated by the addition of methyl chloride at 85° to 90° C. and 60 to 95 p.s.i.g. for 10 hours in a stirred stainless steel pressure vessel. During the reaction the pressure is held between 80 and 95 p.s.i.g. The pH is initially 13 to 14, but as the reaction commences the pH as measured by pH paper and a continuous flow meter drops. The pH is maintained during reaction in the range of 10 to 12 by the periodic addition of sodium hydroxide (7 ml, 50% NaOH). Methyl chloride (26.3 g) is injected into the pressure vessel in the course of the reaction. At the end of the 10-hour reaction period, any unused methyl chloride is vented, and sodium hydroxide (9.5 ml, 50% NaOH) is added for the hydrolysis. The charge is refluxed for 5½ hours, converting the esters to the desired 2-methoxy-3,6-dichlorobenzoic acid.

EXAMPLE 4

Preparation of 2-Methoxy-3,6-dichlorobenzoic Acid

A. Diazotization

2-Amino-3,6-dichlorobenzoic acid (41 g, 0.2 mole) dissolved in absolute ethyl alcohol (300 ml) is charged into a reaction flask equipped with a thermometer, mechanical stirrer, and dropping funnel. The solution is then cooled to about 0° C., and concentrated hydrochloric acid (20 ml) is added with continuous stirring. Chilled isoamyl nitrite (50 ml, 0.38 mole) is added dropwise over a period of about 10 minutes to the stirred solution, which is maintained at about 0° C. The reaction mixture is kept at about 0° C. for an additional hour to ensure completion of the reaction. After this time urea (10.8 g) is added to the reaction mixture.

B. Hydrolysis

About 200 ml of ethyl ether is added to the diazonium solution, prepared as described above, to effect precipitation of the diazonium salt. This salt is then recovered by filtration and washed with additional ether. The product is then dissolved in water (500 ml) and concentrated sulfuric acid (250 ml), and the resulting solution is heated with continuous stirring to about 105° to 110° C. for a period of about 6 hours. The reaction mixture is then cooled, extracted with ethyl ether, dried over anhydrous magnesium sulfate, and filtered. The ether is stripped from the filtrate to give a residue. The residue is recrystallized from benzene to give the desired 2-hydroxy-3,6-dichlorobenzoic acid.

C. Methylation

2-Hydroxy-3,6-dichlorobenzoic acid (44.4 g) is dissolved in a solution of potassium hydroxide (11.2 g, 0.2 mole) and water (100 ml). The solution is heated to reflux (about 100° C.) and stirred vigorously while dimethyl sulfate (63.1 g, 0.5 mole) is added dropwise. The reaction mixture is then treated with a solution of potassium hydroxide (14.0 g, 0.25 mole) in 25.0 ml of water and refluxed for an additional 2 hours. The reaction mixture is then cooled and acidified to Congo red with hydrochloric acid to precipitate the desired 2-methoxy-3,6-dichlorobenzoic acid.

EXAMPLE 5

Preparation of 2-Methoxy-3,6-dichlorobenzoic Acid

A. Diazotization

2-Amino-3,6-dichlorobenzoic acid (41 g, 0.2 mole) dissolved in tetrahydrofuran (500 ml) is charged into a reaction flask equipped with a thermometer, mechanical stirrer, and dropping funnel. The solution is then cooled to about 0° C., and trichloroacetic acid (0.3 g) is added with continuous stirring. Chilled isoamyl nitrite (50 ml, 0.38 mole) is added dropwise over a period of about 10 minutes to the stirred solution, while the temperature is maintained at about 0° C. utilizing an ice-salt bath. The reaction mixture is then stirred at about 0° C. for an additional hour to ensure completion of the reaction. After this time urea (10.8 g) is added to the reaction mixture.

B. Hydrolysis

About 200 ml of ethyl ether is added to the diazonium solution, prepared as described above, to effect precipitation of the diazonium salt. This salt is then recovered by filtration and washed with addition ether. The product is then dissolved in water (500 ml) and concentrated sulfuric acid (250 ml), and the resulting solution is heated with continuous stirring to about 130° to 145° C. for a period of about 3 to 4 hours. The reaction mixture is then cooled, extracted with ethyl ether, dried over anhydrous magnesium sulfate, and filtered. The ether is stripped from the filtrate to give a residue. The residue is recrystallized from benzene to give the desired 2-hydroxy-3,6-dichlorobenzoic acid.

C. Methylation

2-Hydroxy-3,6-dichlorobenzoic acid (44.4 g), prepared as described above, is dissolved in sodium hydroxide and water, making 189 ml of solution. This material is methylated by the addition of methyl chloride at 85° to 90° C. and 60 to 95 p.s.i.g. for 10 hours in a stirred stainless steel pressure vessel. During the reaction the pressure is held between 80 and 95 p.s.i.g. The pH is initially 13 to 14, but as the reaction commences the pH as measured by pH paper and a continuous flow meter drops. The pH is maintained during the reaction in the range of 10 to 12 by the periodic addition of sodium hydroxide (7 ml, 50% NaOH). Methyl chloride (26.3 g) is injected into the pressure vessel in the course of the reaction. At the end of the 10-hour reaction period, any unused methyl chloride is vented, and sodium hydroxide (9.5 ml, 50% NaOH) is added for the hydrolysis. The charge is refluxed for 5½ hours, converting the esters to the desired 2-methoxy-3,6-dichlorobenzoic acid.

EXAMPLE 6

Preparation of 2-Methoxy-3,6-dichlorobenzoic Acid

A. Diazotization

2-Amino-3,6-dichlorobenzoic acid (50 g, 0.24 mole) is dissolved in water (1 l.) and 2 N sodium hydroxide (130 ml, 0.26 mole). Sodium nitrite (20 g, 0.28 mole) is added to the solution, and the mixture is stirred until all of the added sodium nitrite dissolves. The resulting solution is then added in 25 ml portions with vigorous shaking to a solution of 6 N hydrochloric acid (200 ml) in water (100 ml), which is maintained at about 0° C. utilizing an ice-salt bath. The reaction mixture is then stirred at 0° C. for an additional hour to ensure completion of the reaction. After this time urea (0.3 g) is added to the reaction mixture.

B. Methanolysis

About 200 ml of ethyl ether is added to the diazonium solution, prepared as described above, to effect precipitation of the diazonium salt. This salt is then recovered and washed with additional ether. The recovered product is dissolved in about a 10-fold excess of absolute methyl alcohol and warmed on a water bath until nitrogen ceases to evolve. The solvent is then stripped in vacuo from the reaction mixture to give a residue. The residue is then extrated with ethyl ether, dried over anhydrous magnesium sulfate, and filtered. Removal of the ether gives the desired product, 2-methoxy-3,6-dichlorobenzoic acid.

EXAMPLE 7

Preparation of 2-Methoxy-3,6-dichlorobenzoic Acid

A. Diazotization

2-Amino-3,6-dichlorobenzoic acid (41 g, 0.2 mole) dissolved in absolute ethyl alcohol (300 ml) is charged into a reaction flask equipped with a thermometer, mechanical stirrer, and dropping funnel. The solution is then cooled to about 0° C., and concentrated hydrochloric acid (20 ml) is added with continuous stirring. Chilled isoamyl nitrite (50 ml, 0.38 mole) is added dropwise over a period of about 10 minutes to the stirred solution, which is maintained at about 0° C. The reaction mixture is then stirred at about 0° C. for an additional hour to ensure completion of the reaction. After this time urea (10.8 g) is added to the reaction mixture.

B. Methanolysis

About 200 ml of ethyl ether is added to the diazonium solution, prepared as described above, to effect precipitation of the diazonium salt. This salt is then recovered and washed with additional ether. The recovered product is dissolved in about a 10-fold excess of absolute methyl alcohol and warmed on a water bath until nitrogen ceases to evolve. The solvent is then stripped in vacuo from the reaction mixture to give a residue. The residue is then extracted with ethyl ether, dried over anhydrous magnesium sulfate, and filtered. Removal of the ether gives the desired product, 2-methoxy-3,6-dichlorobenzoic acid.

I claim:

1. A process for the production of 2-methoxy-3,6-dichlorobenzoic acid which comprises reacting 2-amino-3,6-dichlorobenzoic acid with a minimum of one mole of nitrous acid for each mole of the 2-amino-3,6-dichlorobenzoic acid to form the corresponding diazonium salt, hydrolyzing the diazonium salt, hydrolyzing the diazonium salt to form 2-hydroxy-3,6-dichlorobenzoic acid and methylating said hydroxy acid.

2. The process of claim 1 wherein the reaction of 2-amino-3,6-dichlorobenzoic acid with nitrous acid comprises dissolving said benzoic acid in an inert reaction medium and thereafter preparing the nitrous acid in situ by combining a nitrosating agent and an acid selected from the group consisting of mineral acids, lower alkanoic acids and perhalo(lower)alkanoic acids.

3. The process of claim 1 wherein hydrolyzing the diazonium salt comprises reacting said salt with water in the presence of a strong mineral acid.

4. The process of claim 1 wherein methylating the hydroxy acid comprises reacting said acid with methyl chloride in an aqueous reaction medium at a pH greater than 10.

5. The process of claim 1 wherein methylating the hydroxy acid comprises reacting said acid with an excess molar amount of dimethyl sulfate in an aqueous reaction medium and in the presence of at least 2 molar amounts of an alkali metal hydroxide per mole of hydroxy acid.

6. A process for the production of 2-methoxy-3,6-dichlorobenzoic acid which comprises (a) dissolving 2-amino-3,6-dichlorobenzoic acid in an inert organic reaction medium and thereafter preparing nitrous acid in situ by combining a nitrosating agent and an acid selected from the group consisting of mineral acids, lower alkanoic acids, and perhalo(lower)alkanoic acids, in said reaction medium while maintaining the reaction mixture at a temperature below 8° C. to form the 3,6-dichloro-2-carboxybenzenediazonium salt; (b) hydrolyzing said diazonium salt with water in the presence of a strong mineral acid to form 2-hydroxy-3,6-dichlorobenzoic acid and (c) methylating said hydroxy acid by methylating it with methyl chloride in an aqueous medium and at a pH greater than 10.

7. The process of claim 6 wherein the nitrosating agent of step (a) is selected from the group consisting of nitrous fumes, sodium nitrite, potassium nitrite, methyl nitrite, ethyl nitrite, propyl nitrite, isopropyl nitrite, n-butyl nitrite, sec-butyl nitrite, isobutyl nitrite, amyl nitrite, sec-amyl nitrite and isoamyl nitrite.

8. The process of claim 6 wherein in step (a) the mineral acid is hydrochloric acid or sulfuric acid, and the lower alkanoic acid is selected from the group consisting of acetic acid, propionic acid and butanoic acid, and the perhalo(lower)alkanoic acid is selected from the group consisting of trichloroacetic acid, trifluoroacetic acid and trifluorobutanoic acid.

9. The process of claim 6 wherein the temperature of the reaction mixture in step (a) is maintained between about −20° and 5° C.

10. The process of claim 6 wherein hydrolyzing the diazonium salt comprises heating said salt in an aqueous medium in the presence of a strong mineral acid at a temperature of from 30° to about 175° C.

11. The process of claim 10 wherein the mineral acid is sulfuric acid and the reaction temperature ranges from 85° to 155° C.

12. The process of claim 6 wherein methylating the 2-hydroxy-3,6-dichlorobenzoic acid comprises reacting a molar amount of said hydroxy acid with at least 2 molar amounts of methyl chloride in an aqueous basic reaction medium having a pH greater than 10 at a temperature ranging from 75° to 150° C. and a pressure of from about 50 pounds to about 150 pounds per square inch.

* * * * *